US006248918B1

(12) United States Patent
Shibasaki et al.

(10) Patent No.: US 6,248,918 B1
(45) Date of Patent: Jun. 19, 2001

(54) OPTICALLY ACTIVE BINAPHTHYL COMPOUND AND METHOD FOR PRODUCING AN OPTICALLY ACTIVE CYANOHYDRIN COMPOUND EMPLOYING THE BINAPHTHYL COMPOUND

(75) Inventors: Masakatsu Shibasaki; Motomu Kanai; Yoshitaka Hamashima, all of Tokyo (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 0 days.

(21) Appl. No.: 09/410,747

(22) Filed: Oct. 1, 1999

(30) Foreign Application Priority Data

Dec. 28, 1998 (JP) .................................................. 10-372358

(51) Int. Cl.[7] ...................... C07C 253/00; C07D 307/02; C07F 15/00; C07F 9/02
(52) U.S. Cl. ............................ 558/315; 549/491; 556/14; 568/15
(58) Field of Search ................................ 556/14; 558/315; 568/15

(56) References Cited

PUBLICATIONS

Hamashima, Y. et al. A New Bifunctional Asymmetric Catalysis: An Effcient Catalytic Asymmetric Cyanosilylation of Aldehydes Journal of Organic Chemistry 121(1999): pp. 2641–2642.*

* cited by examiner

*Primary Examiner*—Deborah C. Lambkin
(74) *Attorney, Agent, or Firm*—Oblon, Spivak, McClelland, Maier & Neustadt, P.C.

(57) ABSTRACT

An optically active binaphthyl compound of the formula (1):

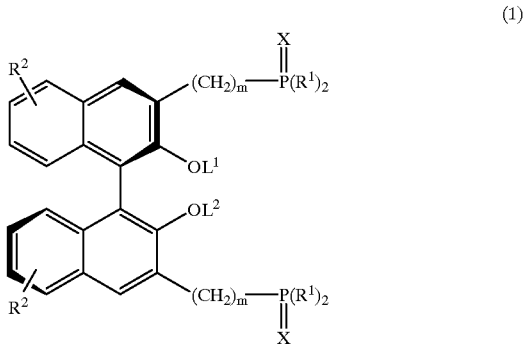

wherein $R^1$ is a $C_{1-6}$ alkyl group, an aryl group or an aryl $C_{1-6}$ alkyl group, X is an oxygen atom or a sulfur atom, $R^2$ is a hydrogen atom, a $C_{1-6}$ alkyl group, a $C_{2-6}$ alkenyl group, a $C_{2-6}$ alkynyl group or a halogen atom, each of $L^1$ and $L^2$ is a hydrogen atom, or $L^1$ and $L^2$ together form MY wherein M is a rare earth element or a Group 13 element, and Y is a $C_{1-6}$ alkoxy group, a $C_{1-6}$ alkylcarbonyloxy group or a halogen atom, and m is an integer of from 1 to 3.

12 Claims, No Drawings

OPTICALLY ACTIVE BINAPHTHYL COMPOUND AND METHOD FOR PRODUCING AN OPTICALLY ACTIVE CYANOHYDRIN COMPOUND EMPLOYING THE BINAPHTHYL COMPOUND

BACKGROUND OF THE INVENTION

1. Field of the Invention

The present invention relates to an optically active metal complex catalyst compound showing excellent stereoselectivity as it has in its molecule two moieties i.e. a Lewis acid moiety for activating an electrophile and a Lewis base moiety for fixing the position of a nucleophile, an asymmetric ligand compound constituting said catalyst compound, and a method for producing an optically active cyanohydrin compound employing said catalyst compound.

2. Discussion of Background

Optically active substances have been used in many products or intermediates for agricultural chemicals, pharmaceuticals, etc., and the demand for synthesis for optically active substances at an industrially practical level has been increasing year after year.

For the preparation of an optically active substance by an asymmetric reaction, a catalytic asymmetric synthesis is most efficient and industrially superior, whereby a large amount of an optically active substance can be obtained by using a small amount of an asymmetric source.

As such a catalytic asymmetric synthesis, a method has been known wherein a complex having a rare earth element or a Group 13 element (Al or Ga) as the central metal and further containing an alkali metal and a binaphthol as an asymmetric ligand, is used as a catalyst, whereby it has been successful to efficiently synthesize various optically active substances.

It is believed that such a complex exhibits high stereoselectivity, as the central metal serves as a Lewis acid to activate an electrophile, and the alkali metal binaphthoxide moiety serves as a Brønsted base to fix the position of the nucleophile.

Namely, the above complex makes such excellent stereoselectivity possible as it has, in its molecule, two moieties i.e. the Lewis acid moiety for activating the electrophile and the Brønsted base moiety for fixing the position of the nucleophile. However, with respect to an optical active metal complex catalyst having in its molecules two moieties i.e. a Lewis acid moiety for activating the electrophile and a Lewis base moiety for fixing the position of the nucleophile, there has been no report on a product having a high applicability.

On the other hand, with respect to an optically active cyanohydrin compound, many chemical and enzymatic syntheses have been reported, but little has been known with respect to one which is commonly applicable to any type of a substrate to be used.

Especially, nothing has been reported on an efficient asymmetric catalyst containing an aliphatic aldehyde or an aromatic aldehyde as the substrate.

SUMMARY OF THE INVENTION

The present inventors have conducted an extensive study and as a result, have found an optically active metal complex catalyst compound having in its molecule two moieties i.e. a Lewis acid moiety for activating an electrophile and a Lewis base moiety for fixing the position of a nucleophile, and have further found it possible to obtain an optically active cyanohydrin compound from an aldehyde compound in good chemical yield and good optical yield by using such a compound as a catalyst. The present invention has been accomplished on the basis of these discoveries.

Namely, the present invention provides an optically active binaphthyl compound of the formula (1):

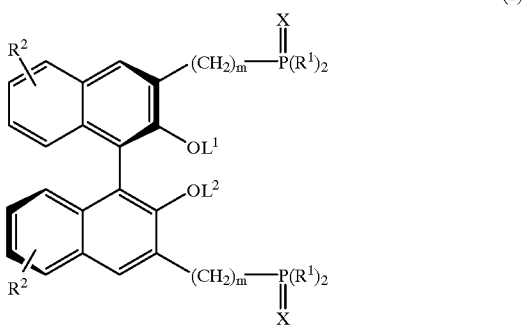

(1)

wherein $R^1$ is a $C_{1-6}$ alkyl group, an aryl group or an aryl $C_{1-6}$ alkyl group, X is an oxygen atom or a sulfur atom, $R^2$ is a hydrogen atom, a $C_{1-6}$ alkyl group, a $C_{2-6}$ alkenyl group, a $C_{2-6}$ alkynyl group or a halogen atom, each of $L^1$ and $L^2$ is a hydrogen atom, or $L^1$ and $L^2$ together form MY wherein M is a rare earth element or a Group 13 element, and Y is a $C_{1-6}$ alkoxy group, a $C_{1-6}$ alkylcarbonyloxy group or a halogen atom, and m is an integer of from 1 to 3.

Further, the present invention provides a method for producing an optically active cyanohydrin compound of the formula (3):

(3)

wherein $R^3$ is a $C_{1-6}$ alkyl group, an aryl group, an aryl $C_{1-6}$ alkyl group, a $C_{2-6}$ alkenyl group, an aryl $C_{2-6}$ alkenyl group, a $C_{2-6}$ alkynyl group, an aromatic heterocyclic group or a non-aromatic heterocyclic group, which comprises reacting an aldehyde compound of the formula (2):

$R^3$CHO (2)

wherein $R^3$ is as defined above, with trimethylsilylcyanide in the presence of the optically active compound of the formula (1) wherein $L^1$ and $L^2$ together form MY wherein M and Y are as defined above.

DETAILED DESCRIPTION OF THE PREFERRED EMBODIMENTS

Now, the present invention will be described in detail.

Firstly, terms used for the substituents of $R^1$, $R^2$, $R^3$, $R^4$, $R^5$, $R^6$, m, X, $L^1$ and $L^2$, will be described.

In this specification, "n" means normal, "i" iso, "s" secondary, "t" tertiary, "c" cyclo, "o" ortho, "m" meta, "p" para, "Et" ethyl, "Bu" butyl, "Oct" octyl, "Ph" phenyl, "Ms" methanesulfonyl, "Ts" p-toluenesulfonyl, and "MOM" methoxymethyl.

The rare earth element includes lanthanum (La), cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm), ytterbium (Y) and lutetium (Lu).

The Group 13 element includes aluminum (Al) and gallium (Ga).

The $C_{1-6}$ alkyl group includes, for example, a methyl group, an ethyl group, a n-propyl group, an i-propyl group, a c-propyl group, a n-butyl group, an i-butyl group, a s-butyl group, a t-butyl group, a c-butyl group, a n-pentyl group, a 2-pentyl group, a 3-pentyl group, an i-pentyl group, a neopentyl group, a t-pentyl group, a c-pentyl group, a n-hexyl group, a 2-hexyl group, a 3-hexyl group, a c-hexyl group, a 1-methyl-1-ethyl-n-propyl group, a 1,1,2,-trimethyl-n-propyl group, a 1,2,2-trimethyl-n-propyl group and a 3,3-dimethyl-n-butyl group. The $C_{1-8}$ alkyl group includes, for example, a n-heptyl group and a n-octyl group, in addition to the above alkyl groups.

The $C_{2-6}$ alkenyl group includes, for example, an ethenyl group, a 1-propenyl group, a 2-propenyl group, a 1-butenyl group, a 2-butenyl group, a 3-butenyl group, a 1-pentenyl group, a 2-pentenyl group, a 3-pentenyl group, a 4-pentenyl group, a 1-hexenyl group, a 2-hexenyl group, a 3-hexenyl group, a 4-hexenyl group and a 5-hexenyl group.

The $C_{2-6}$ alkynyl group includes, for example, an ethynyl group, a 1-propynyl group, a 2-propynyl group, a 1-butynyl group, a 2-butynyl group, a 3-butynyl group, a 1-pentynyl group, a 2-pentynyl group, a 3-pentynyl group, a 4-pentynyl group, a 1-hexynyl group, a 2-hexynyl group, a 3-hexynyl group, a 4-hexynyl group and a 5-hexynyl group.

The $C_{1-6}$ alkoxy group includes, for example, a methoxy group, an ethoxy group, a n-propoxy group, an i-propoxy group, a c-propoxy group, a n-butoxy group, an i-butoxy group, a s-butoxy group, a t-butoxy group, a c-butoxy group, a n-pentyloxy group and a n-hexyloxy group. The $C_{1-6}$ alkylcarbonyloxy group includes, for example, a methylcarbonyloxy group, an ethylcarbonyloxy group, a n-propylcarbonyloxy group, an i-propylcarbonyloxy group, a n-butylcarbonyloxy group, an i-butylcarbonyloxy group, a s-butylcarbonyloxy group, a t-butylcarbonyloxy group, a 1-pentylcarbonyloxy group, a 2-pentylcarbonyloxy group, a 3-pentylcarbonyloxy group, a i-pentylcarbonylxoy group, a neopentylcarbonyloxy group, a t-pentylcarbonyloxy group, a 1-hexylcarbonyloxy group, a 2-hexylcarbonyloxy group, a 3-hexylcarbonyloxy group, a 1-methyl-n-pentylcarbonyloxy group, a 1,1,2-trimethyl-n-propylcarbonyloxy group, a 1,2,2-trimethyl-n-propylcarbonyloxy group and a 3,3-dimethyl-n-butylcarbonyloxy group.

The aryl $C_{2-6}$ alkenyl group includes, for example, a 1-phenylethenyl group, a 2-phenylethenyl group, a 1-phenyl-1-propenyl group, a 2-phenyl-1-propenyl group, a 3-phenyl-1-propenyl group, a 1-phenyl-2-propenyl group, a 2-phenyl-2-propenyl group, a 3-phenyl-2-propenyl group, a 1-phenyl-1-butenyl group, a 2-phenyl-1-butenyl group, a 3-phenyl-1-butenyl group, a 4-phenyl-1-butenyl group, a 1-phenyl-2-butenyl group, a 2-phenyl-2-butenyl group, a 3-phenyl-2-butenyl group, a 4-phenyl-2-butenyl group, a 3-phenyl-3-butenyl group, a 2-phenyl-3-butenyl group, a 3-phenyl-3-butenyl group, a 4-phenyl-3-butenyl group, a 5-phenyl-1-pentenyl group, a 5-phenyl-2-pentenyl group, a 5-phenyl-3-pentenyl group, a 5-phenyl-4-pentenyl group, a 6-phenyl-1-hexenyl group, a 6-phenyl-2-hexenyl group, a 6-phenyl-3-hexenyl group, a 6-phenyl-4-hexenyl group and a 6-phenyl-5-hexenyl group.

The aryl group includes, for example, a phenyl group, an o-methylphenyl group, a m-methylphenyl group, a p-methylphenyl group, an o-chlorophenyl group, a m-chlorophenyl group, a p-chlorophenyl group, an o-fluorophenyl group, a p-fluorophenyl group, an o-methoxyphenyl group, a p-methoxyphenyl group, a p-nitrophenyl group, a p-cyanophenyl group, an α-naphthyl group, a β-naphthyl group, an o-biphenylyl group, a m-biphenylyl group, a p-biphenylyl group, a 1-anthryl group, a 2-anthryl group, a 9-anthryl group, a 1-phenanthryl group, a 2-phenanthryl group, a 3-phenanthryl group, a 4-phenanthryl group and a 9-phenanthryl group.

The aryl $C_{1-6}$ alkyl group includes, for example, a benzyl group, an o-methylbenzyl group, a m-methylbenzyl group, a p-methylbenzyl group, an o-chlorobenzyl group, a m-chlorobenzyl group, a p-chlorobenzyl group, an o-fluorobenzyl group, a p-fluorobenzyl group, an o-methoxybenzyl group, a p-methoxybenzyl group, a p-nitrobenzyl group, a p-cyanobenzyl group, a phenethyl group, an o-methylphenethyl group, a m-methylphenethyl group, a p-methylphenethyl group, an o-chlorophenethyl group, a m-chlorophenethyl group, a p-chlorophenethyl group, an o-fluorophenethyl group, a p-fluorophenethyl group, an o-methoxyphenethyl group, a p-methoxyphenethyl group, a p-nitrophenethyl group, a p-cyanophenethyl group, a 3-phenylpropyl group, a 4-phenylbutyl group, a 5-phenylpentyl group, a 6-phenylhexyl group, an α-naphthylmethyl group, a β-naphthylmethyl group, an o-biphenylylmethyl group, a m-biphenylylmethyl group, a p-biphenylylmethyl group, a 1-anthrylmethyl group, a 2-anthrylmethyl group, a 9-anthrylmethyl group, a 1-phenanthrylmethyl group, a 2-phenanthrylmethyl group, a 3-phenanthrylmethyl group, a 4-phenanthrylmethyl group, a 9-phenanthrylmethyl group, an a-naphthylethyl group, a β-naphthylethyl group, an o-biphenylylethyl group, a m-biphenylylethyl group, a p-biphenylylethyl group, a 1-anthrylethyl group, a 2-anthrylethyl group, a 9-anthrylethyl group, a 1-phenanthrylethyl group, a 2-phenanthrylethyl group, a 3-phenanthrylethyl group, a 4-phenanthrylethyl group and a 9-phenanthrylethyl group.

The aromatic heterocyclic group may, for example, be a 5- to 7-membered monocyclic heterocyclic group or a 8-to 10-membered condensed bicyclic heterocyclic group, which may contain from 1 to 3 atoms selected from oxygen, nitrogen and sulfur atoms.

The aromatic heterocyclic group includes, for example, a 2-thienyl group, a 3-thienyl group, a 2-furyl group, a 3-furyl group, a 2-pyranyl group, a 3-pyranyl group, a 4-pyranyl group, a 2-benzofuranyl group, a 3-benzofuranyl group, a 4-benzofuranyl group, a 5-benzofuranyl group, a 6-benzofuranyl group, a 7-benzofuranyl group, a 1-isobenzofuranyl group, a 4-isobenzofuranyl group, a 5-isobenzofuranyl group, a 2-benzothienyl group, a 3-benzothienyl group, a 4-benzothienyl group, a 5-benzothienyl group, a 6-benzothienyl group, a 7-benzothienyl group, a 1-isobenzothienyl group, a 4-isobenzothienyl group, a 5-isobenzothienyl group, a 2-chromenyl group, a 3-chromenyl group, a 4-chromenyl group, a 5-chromenyl group, a 6-chromenyl group, a 7-chromenyl group, a 8-chromenyl group, a 1-pyrrolyl group, a 2-pyrrolyl group, a 3-pyrrolyl group, a 1-imidazolyl group, a 2-imidazolyl group, a 4-imidazolyl group, a 1-pyrazolyl group, a 3-pyrazolyl group, a 4-pyrazolyl group, a 2-thiazolyl group, a 5-thiazolyl group, a 3-isothiazolyl group, a 4-isothiazolyl group, a 5-isothiazolyl group, a 2-oxazolyl group, a 4-oxazolyl group, a 5-oxazolyl group, a 3-isoxazolyl group, a 4-isoxazolyl group, a 5-isoxazolyl group, a 2-pyridyl group, a 3-pyridyl group, a 4-pyridyl group, a 2-pyrazinyl group, a 2-pyrimidinyl group, a 4-pyrimidinyl group, a 5-pyrimidinyl group, a 3-pyridazinyl group, a 4-pyridazinyl group, a 1-indolizinyl group, a 2-indolizinyl group, a 3-indolizinyl group, a 5-indolizinyl group, a 6-indolizinyl group, a 7-indolizinyl group, a 8-indolizinyl group, a 1-isoindolyl group, a 4-isoindonyl group, a 5-isoindolyl group, a 1-indolyl group, a 2-indolyl group, a 3-indolyl group, a 4-indolyl group, a 5-indolyl group, a 6-indolyl group, a 7-indolyl group, a 1-indazolyl group, a 2-indazolyl group, a 3-indazolyl group, a 4-indazolyl group, a 5-indazolyl group, a 6-indazolyl group, a 7-indazolyl group, a 3-purinyl group, a 2-purinyl group, a 3-purinyl group, a 6-purinyl group, a 7-purinyl group, a 8-purinyl group, a 2-quinolyl group, a 3-quinolyl group, a 4-quinolyl group, a 5-quinolyl group, a 6-quinolyl group, a 7-quinolyl group, a 8-quinolyl group, a 1-isoquinolyl group, a 3-isoquinolyl group, a 4-isoquinolyl group, a 5-isoquinolyl group, a 6-isoquinolyl group, a 7-isoquinolyl group, a 8-isoquinolyl group, a 1-phthalazinyl group, a 5-phthalazinyl group, a 6-phthalazinyl group, a 2-naphthyridinyl group, a 3-naphthyridinyl group, a 4-naphthyridinyl group, a 2-quinoxalinyl group, a 5-quinoxalinyl group, a 6-quinoxalinyl group, a 2-quinazolinyl group, a 4-quinazolinyl group, a 5-quinazolinyl group, a 6-quinazolinyl group, a 7-quinazolinyl group, a 8-quinazolinyl group a 3-cinnolinyl group, a 4-cinnolinyl group, a 5-cinnolinyl group, a 6-cinnolinyl group, a 7-cinnolinyl group, a 8-cinnolinyl group, a 2-ptenydinyl group, 4-ptenydinyl, group, a 6-ptenydinyl group, a 7-ptenydinyl group and a 3-furazanyl group.

The non-aromatic heterocyclic group may, for example, be a 5- to 7-monocyclic heterocyclic group, or a 6- to 10-membered condensed bicyclic heterocyclic group, which contains from 1 to 3 atoms selected from oxygen, nitrogen and sulfur atoms.

The non-aromatic heterocyclic group includes, for example, a 2-tetrahydrofuranyl group, a 3-tetrahydrofuranyl group, a 2-tetrahydropyranyl group, a 3-tetrahydropyranyl group, a 4-tetrahydropyranyl group, a 1-pyrrolidinyl group, a 2-pyrrolidinyl group, a 3-pyrrolidinyl group, a 1-pyrrolinyl group, a 2-pyrrolinyl group, a 3-pyrrolinyl group, a 4-pyrrolinyl group, a 5-pyrrolinyl group, a 1-imidazolidinyl group, a 2-imidazolidinyl group, a 4-imidazolidinyl group, a 1-imidazolinyl group, a 2-imidazolinyl group, a 4-imidazolinyl group, a 1-pyrazolidinyl group, a 3 - pyrazolidinyl group, a 4-pyrazolidinyl group, a 1-pyrazolinyl group, a 2-pyrazolinyl group, a 3-pyrazolinyl group, a 4-pyrazolinyl group, a 5-pyrazolinyl group, a 1-piperidyl group, a 2-piperidyl group, a 3-piperidyl group, a 4-piperidyl group, a 1-piperazinyl group, a 2-piperazinyl group, a 3-piperazinyl group, a 1-indolinyl group, a 2-indolinyl group, a 3-indolinyl group, a 4-indolinyl group, a 5-indolinyl group, a 6-indolinyl group, a 7-indolinyl group, a 1-isoindolinyl group, a 2-isoindolinyl group, a 4-isoindolinyl group, a 5-isoindolinyl group, a 2-quinuclidinyl group, a 3-quinuclidinyl group, a 4-quinuclidinyl group, a 2-morpholinyl group, a 3-morpholinyl group, a 4-morpholinyl group, a 1-azetidinyl group, a 2-azetidinyl group, a 3-azetidinyl group, a 1-azetidinonyl group, a 3-azetidinonyl group and a 4-azetidinonyl group.

The halogen atom includes a fluorine atom, a chlorine atom, a bromine atom and an iodine atom.

Now, preferred $R^1$, $R^2$, $R^3$, $R^4$, $R^5$, $R^6$, m, X, $L^1$ and $L^2$ will be described.

As preferred $R^1$, a phenyl group may be mentioned.

As preferred $R^2$, a hydrogen atom may be mentioned.

As preferred $R^3$, $(CH_2)_2Ph$, $CH(CH_3)_2$, Ph, $(CH_2)_5CH_3$, $CH(CH_2CH_3)_2$, $CH=CH(CH_2)_3CH_3$, $CH=CHPh$, $C(CH_3)_2CH_2Ph$, a cyclohexyl group, a p-methylphenyl group or a 2-furyl group may be mentioned.

As preferred $R^4$, $R^5$ and $R^6$ which are independent of one another, $CH_3$, $(CH_2)_3CH_3$, $(CH_2)_7CH_3$ or Ph may be mentioned.

As preferred m, 1 or 2 may be mentioned.

As preferred X, an oxygen atom may be mentioned.

As preferred $L^1$ and $L^2$ which are independent of each other, a hydrogen atom may be mentioned, or $L^1$ and $L^2$ may together form AlCl.

Now, the synthesis of the optically active binaphthyl compound of the formula (1) will be described.

Among optical active binaphthyl compounds represented by the formula (1), a synthesis of an optically active binaphthyl compound of the formula (6) wherein each of $L^1$ and $L^2$ is a hydrogen atom, is shown by reaction scheme 1.

Reaction scheme 1

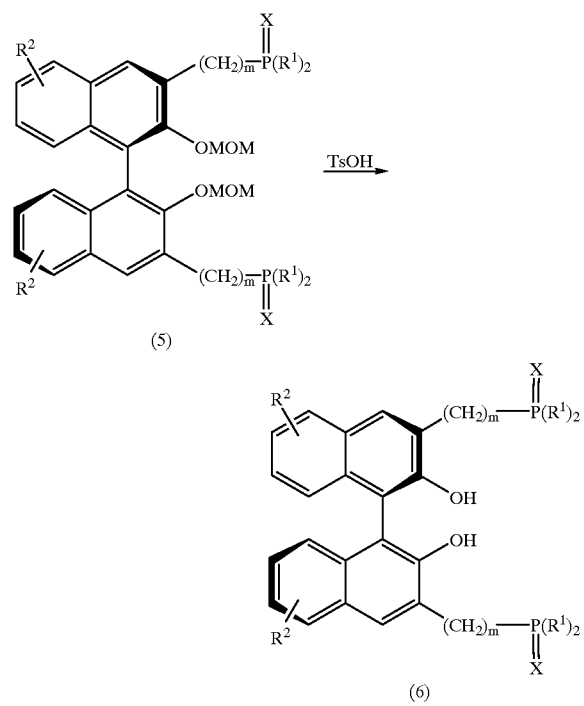

(5)

(6)

wherein $R^1$, $R^2$, m and X are as defined above.

By reacting p-toluenesulfonic acid to a compound of the formula (5), the desired compound of the formula (6) can be prepared.

The solvent for the reaction may be any solvent so long as it is inert to the reaction, and for example, an aromatic solvent such as benzene or toluene, an ether solvent such as tetrahydrofuran or 1,4-dioxane, an amide solvent such as formamide, N,N-dimethylformamide, N,N-dimethylacetamide or N-methylpyrrolidone, an alcohol solvent such as methanol, ethanol or propanol, a halogen type solvent such as chloroform, methylene chloride or ethylene dichloride, other solvents such as acetonitrile and dimethylsulfoxide, water, or a solvent mixture thereof, may be mentioned.

The reaction temperature may be within a range of from 0° C. to the boiling point of the solvent used for the reaction. However, it is preferably from 20 to 80° C.

The reaction time varies depending upon the temperature for the reaction, but it is usually from 1 to 100 hours, preferably from 3 to 30 hours.

The amount of p-toluenesulfonic acid is usually within a range of from 10 to 200 mol %, preferably from 30 to 150 mol %, relative to the substrate.

Among optically active binaphthyl compounds represented by the formula (1), a synthesis of an optically active binaphthyl compound of the formula (8) wherein $L^1$ and $L^2$ together form MY, is shown by reaction scheme 2.

Reaction scheme 2

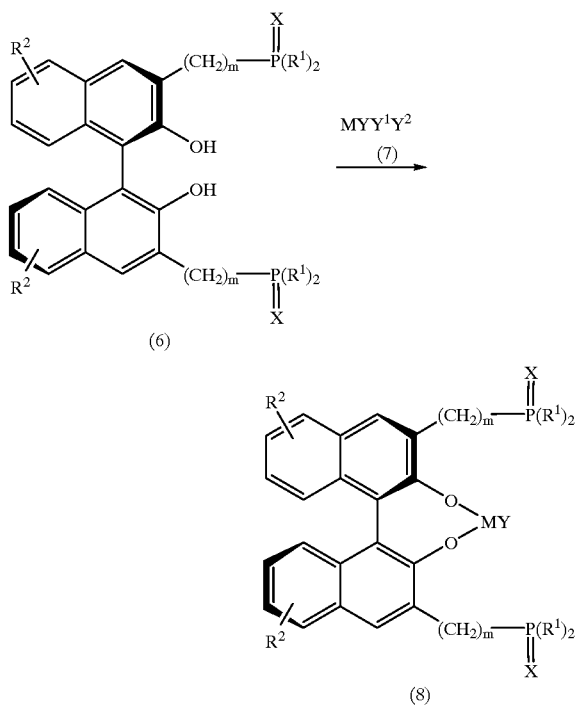

wherein $R^1$, $R^2$, M, Y, m and X are as defined above, and each of $Y^1$ and $Y^2$ which are independent of each other, is a $C_{1-6}$ alkyl group, a $C_{1-6}$ alkoxy group, a $C_{1-6}$ alkylcarbonyloxy group or a halogen atom.

By reacting a trivalent metal compound (7) to the compound of the formula (6), it is possible to obtain the desired compound of the formula (8).

The solvent for the reaction may be any solvent so long as it is inert to the reaction, and for example, a saturated aliphatic solvent such as n-pentane, n-hexane, cyclohexane or petroleum ether, an aromatic solvent such as benzene or toluene, an ether solvent such as tetrahydrofuran or 1,4-dioxane, a halogen type solvent such as chloroform, methyl chloride or ethylene dichloride, or a solvent mixture thereof, may be mentioned.

The reaction temperature may be within a range of from −10° C. to the boiling point of the solvent used for the reaction. However, the temperature is preferably from 0 to 50° C.

The reaction time varies depending upon e.g. the temperature for the reaction, but is usually from 0.1 to 10 hours, preferably from 0.5 to 3 hours.

The amount of the trivalent metal compound (7) may be within a range of from 0.1 to 2 equivalents, preferably from 0.5 to 1.2 equivalents, relative to the substrate.

It is advisable that the instruments, the solvents, etc., are sufficiently dried before use, and the reaction is carried out in a stream of an inert gas such as argon gas.

When the obtained compound of the formula (8) is used as a catalyst for the production of an optically active cyanohydrin compound from an aldehyde compound, the reaction solution is preferably employed as it is, for the production of an optically active cyanohydrin compound, without isolating the compound of the formula (8).

Further, in a case where a phosphine oxide (4) is added to the reaction system to produce an optically active cyanohydrin, it is preferred to add the phosphine oxide (4) beforehand when the compound of the formula (8) is to be prepared.

Now, a synthesis of the compound of the formula (5) as an intermediate for the compound of the formula (6), will be described.

Among compounds represented by the formula (5), a synthesis of a compound of the formula (14) wherein m is 1, is shown by reaction scheme 3.

Reaction scheme 3

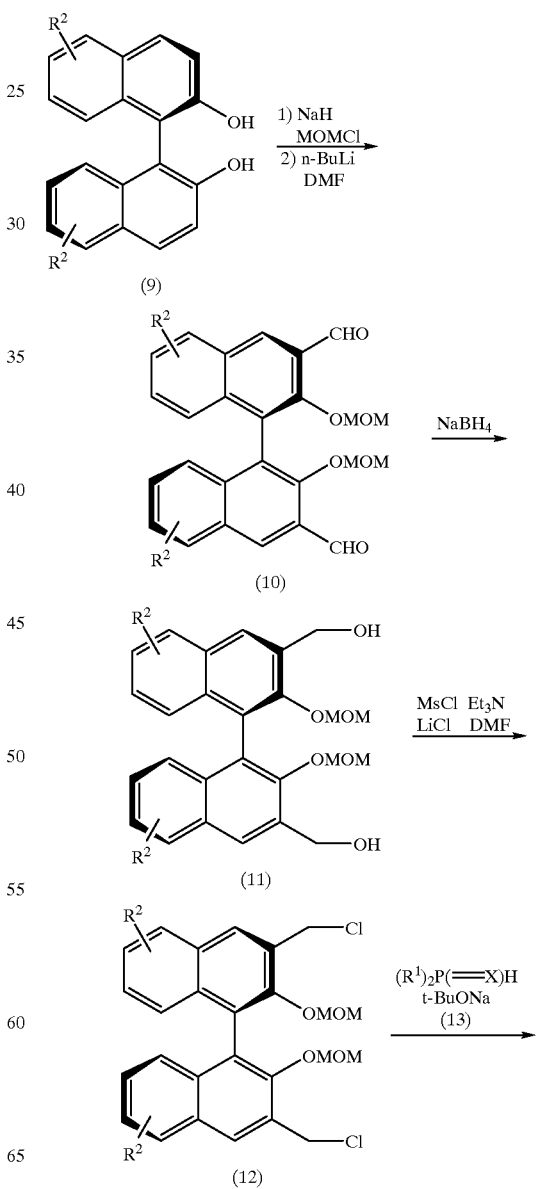

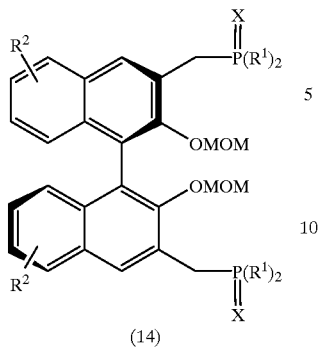

(14)

wherein R¹, R² and X are as defined above.

In the presence of sodium hydride, methoxymethyl chloride is reacted to an optically active binaphthol (9) for methoxymethylation, followed by lithium-modification with n-butyl lithium and formylation with dimethylformamide to obtain a diformyl compound (10).

The diformyl compound (10) is reacted with sodium boron hydride to reduce formyl groups to obtain a diol compound (11).

In the presence of trimethylamine, the diol compound (11) is reacted with methanesulfonyl chloride for methanesulfonylation, followed by a reaction with lithium chloride to obtain a dichloro compound (12).

The dichloro compound (12) is reacted with a phosphine oxide or a phosphine sulfide represented by the formula (13) in the presence of sodium t-butoxide to obtain a compound of the formula (14) which is a compound of the formula (5) wherein m is 1.

A synthesis of a compound of the formula (18) which is a compound of the formula (5) wherein m is 2, is shown by reaction scheme 4.

Reaction scheme 4

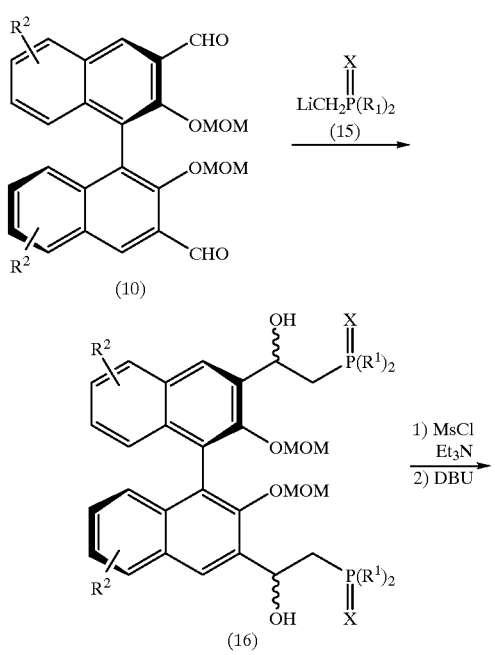

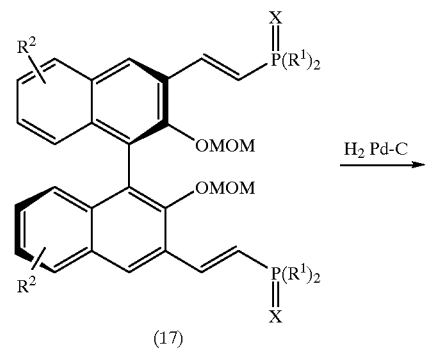

(17)

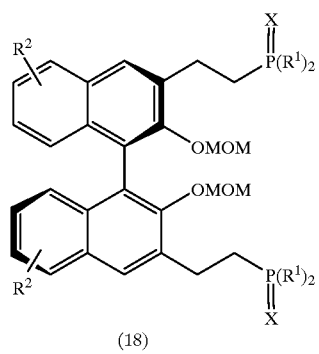

(18)

wherein R¹, R² and X are as defined above.

A lithium reagent of the formula (15) is reacted to a diformyl compound (10) to obtain a compound of the formula (16).

Methanesulfonyl chloride is reacted to the compound of the formula (16) for methanesulfonylation, followed by a reaction with DBU (1,8-diazabicyclo[5,4,0]undec-7-ene) to obtain a compound of the formula (17).

The compound of the formula (17) is treated with a catalytic amount of palladium-carbon in a hydrogen stream, to obtain a compound of the formula (18) which is a compound of the formula (5) wherein m is 2.

A synthesis of a compound of the formula (23) which is a compound of the formula (5) wherein m is 3, is shown by reaction scheme 5.

Reaction scheme 3

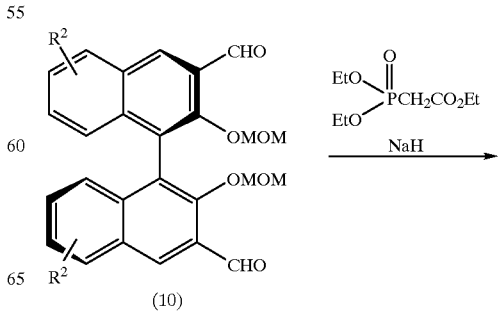

(10)

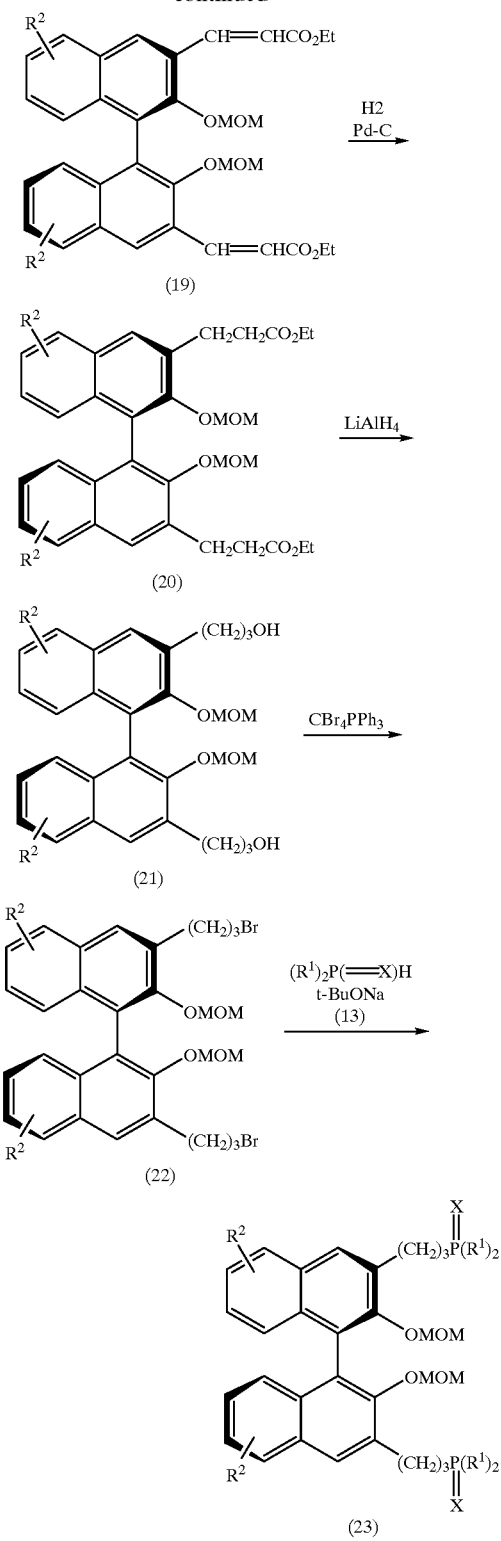

wherein $R^1$, $R^2$ and x are as defined above.

Ethyl diethylphosphonoacetate is reacted to a diformyl compound (10) in the presence of sodium hydride to obtain a compound of the formula (19).

The compound of the formula (19) is treated with a catalytic amount of palladium-carbon in a hydrogen stream to obtain a compound of the formula (20).

The compound of the formula (20) is reduced with lithium aluminum hydride to obtain a diol compound of the formula (21).

Carbon tetrabromide is reacted to the compound of the formula (21) in the presence of triphenylphosphine to obtain a dibromo compound of the formula (22).

A phosphine oxide or a phosphine sulfide of the formula (13) is reacted to the dibromo compound (22) in the presence of sodium t-butoxide to obtain a compound of the formula (23) which is a compound of the formula (5) wherein m is 3.

Now, the process for producing an optically active cyanohydrin compound will be described.

Reaction scheme 6

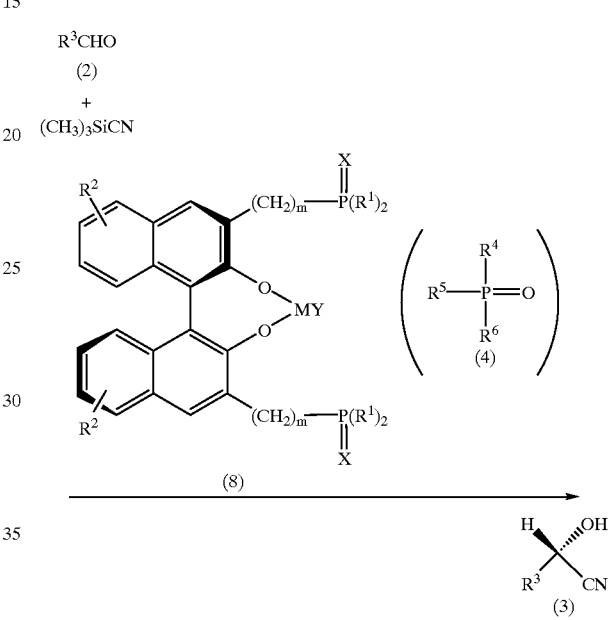

An aldehyde compound of the formula (2) is added to a compound of the formula (8) prepared by reaction scheme 2, to a solution containing the compound of the formula (8) or to a solution containing the compound of the formula (8) and a phosphine oxide of the formula (4). To this solution, trimethylsilylcyanide ($(CH_3)_3SiCN$) is dropwise added to obtain the desired optically active cyanohydrin compound of the formula (3).

The amount of the compound of the formula (8) is usually from 0.1 to 100 mols, preferably from 5 to 30 mols, relatively to the aldehyde of the formula (2).

In the case where the reaction is carried out by an addition of a phosphine oxide of the formula (4), the amount of the phosphine oxide is usually from 1 to 20 equivalents, preferably from 3 to 10 equivalents, relative to the compound of the formula (8).

With respect to the type of the phosphine oxide to be used, when an aliphatic aldehyde wherein $R^3$ is $(CH_2)_2Ph$, $CH(CH_3)_2$, $(CH_2)_5CH_3$, $CH(CH_2CH_3)_{21}$ $CH=CH(CH_2)_3CH_3$, $CH=CHPh$, $C(CH_3)_2CH_2Ph$ or a cyclohexyl group, is employed, it is preferred to use a phosphine oxide having a strong Lewis basicity, such as $n-Bu_3P(O)$, and when an aromatic aldehyde wherein $R^3$ is Ph, a p-methylphenyl group or a 2-furyl group, is employed, it is preferred to employ a phosphine oxide having a slightly weak Lewis basicity, such as $CH_3P(O)Ph_2$.

The solvent for the reaction is not particularly limited so long as it is inert to the reaction, and it may, for example, be an aromatic solvent such as benzene, toluene, xylene, mesitylene, chlorobenzene, fluorobenzene or o-dichlorobenzene, an aliphatic hydrocarbon solvent such as n-hexane, cyclohexane, n-octane or n-decane, a halogen type solvent such as chloroform, methylene chloride or ethylene dichloride, or an ether solvent such as tetrahydrofuran, diethyl ether, t-butyl methyl ether or dimethoxyethane, preferably a halogen type solvent, more preferably methylene chloride.

Further, these solvents may be used alone or in combination as a solvent mixture.

The time for dropping trimethylsilylcyanide is usually within a range of from 1 to 50 hours, preferably within a range of from 5 to 20 hours.

Further, at the time of dropping trimethylsilylcyanide, it is advisable to drop it from the top of the reactor so that trimethylsilylcyanide will not crystallize.

The temperature for the reaction is usually within a range of from −100° C. to 50° C., preferably within a range of from −60° C. to 0° C.

The time for the reaction is usually from 0.1 to 1,000 hours, preferably from 10 to 100 hours.

After completion of the reaction, the product is treated with a suitable acid such as dilute hydrochloric acid and then extracted with a suitable solvent such as ethyl acetate. Then, the solvent is concentrated under reduced pressure, followed by separation by e.g. crystallization, silica gel column chromatography or distillation, to isolate the desired optically active cyanohydrin compound.

Now, the present invention will be described in further detail with reference to Examples. However, it should be understood that the present invention is by no means restricted to such specific Examples.

The optical purity was determined by HPLC (column: Daicel Chiralcell OJ, OD, mobile phase: isopropanol-hexane).

REFERENCE EXAMPLE 1
Preparation of 3,3'-diformyl-2-2'-bis(methoxymethyl)-1,1'-binaphthol 10 g (26.7 mmol) of (R)isomer of 2,2'-bis(methoxymethyl)-1,1'-binaphthol was dissolved in 400 ml of diethyl ether, and 53.1 ml (85.5 mmol) of a 1.61 M hexane solution of n-butyl lithium was added at room temperature.

After stirring at room temperature for 2 hours, the mixture was cooled to 0° C., and 7.24 ml (93.5 mmol) of dimethylformamide was dropwise added thereto over a period of 15 minutes.

The mixture was returned to room temperature and further stirred for 2 hours, whereupon it was neutralized with a saturated ammonium chloride aqueous solution and then extracted with ethyl acetate.

The organic layer was washed with water and a saturated sodium chloride aqueous solution and then dried over anhydrous sodium sulfate.

The solvent was distilled off under reduced pressure, and then, the residue was purified by silica gel flush column chromatography (n-hexane:ethyl acetate=10:1 to 5:1) to obtain 9.0 g (78%) of the above-identified compound as a yellow oily substance.

$^1$H NMR(CDCl$_3$)δ 10.55(s, 2H), 8.62(s, 2H), 8.08(dd, J=8.2, 1.2 Hz, 2H), 7.52(ddd, J=9.2,7.05,1.20 Hz, 2H), 7.43(ddd, J=8.2,7.05,1.50 Hz, 2H), 7.22(dd, J=9.2,1.50H z, 2H), 4.71 (d, J=6.1 Hz, 2H), 4.69(d, J=6.1 Hz, 2H),2.88(s, 6H);
$^{13}$C NMR(CDCl$_3$) δ 190.6, 154.0, 136.7, 132.3, 130.3, 129.6, 128.9, 126.3, 126.1, 1 25.9, 100.6, 57.0

REFERENCE EXAMPLE 2
Preparation of 3,3'-bis(hydroxymethyl)-2,2'-bis(methoxymethyl)-1,1'-binaphthol 4.0 g (9.29 mmol) of 3,3'-diformyl-2,2'-bis(methoxymethyl)-1,1'-binaphthol was dissolved in 140 ml of methanol and cooled to 0° C. Then, 700 mg (18.6 mmol) of sodium boron hydride was added thereto.

After neutralizing it with a saturated ammonium chloride aqueous solution, the mixture was concentrated until the amount of the solution became a half.

50 ml of ethyl acetate was added for extraction, and the organic layer was washed with water.

The aqueous layer was further extracted with ethyl acetate (60 ml×4), and the organic layers were put together and washed with a saturated sodium chloride aqueous solution (50 ml×1).

The obtained product was dried over anhydrous sodium sulfate, and then, the solvent was distilled off under reduced pressure. The residue was purified by silica gel flush column chromatography (n-hexane:acetone=3:1) to obtain 92.6% of the above-identified compound as a colorless solid.

$^1$H NMR(CDCl$_3$) δ 8.02(s,2H), 7.91(m,2H), 7.43(ddd, J=8.25, 6.7, 0.9 Hz, 2H), 7.27 (ddd, J=8.25, 7.0, 1.5 Hz, 2H), 7.15(m, 2H), 4.98(d, J=12.8 Hz, 2H), 4.85(d, J=12.8 Hz , 2H), 4.48(d, J=6.1 Hz, 2H), 4.45(d, J=6.1 Hz, 2H), 3.12(s, 6H);
$^{13}$C NMR(CDCl$_3$)δ 153.1, 134.6, 133.7, 130.9, 129.7, 128.2, 126.8, 125.7, 125.4,1 25.2, 99.3, 61.9, 57.1

REFERENCE EXAMPLE 3
Preparation of 3,3'-bis(chloromethyl)-2,2'-bis(methoxymethyl)-1,1'-binaphthol 3.64 g (8.38 mmol) of 3,3'-bis(hydroxymethyl)-2,2'-bis(methoxymethyl)1,1'-binaphthol was dissolved in 60 ml of toluene and cooled to 0° C.

To this solution, 3.24 ml (41.9 mmol) of methanesulfonyl chloride and 8.17 ml (58.6 mmol) of triethylamine were added.

One hour later, 1.78 g (41.9 mmol) of lithium chloride and 60 ml of dimethylformamide were further added and stirred at room temperature until the starting materials disappeared.

This solution was washed with water (20 ml×2), and the separated aqueous layer was further extracted with ethyl acetate (80 ml×3).

The organic layers were put together and washed with a saturated sodium chloride aqueous solution and then dried over anhydrous sodium sulfate.

The solvent was distilled off under reduced pressure, and the residue was purified by silica gel column chromatography (n-hexane:acetone=4:1) to obtain 3.44 g (87%) of the above-identified compound.

$^1$H NMR(CDCl$_3$)δ 8.11(s, 2H), 7.90(d, J=8.25 Hz, 2H), 7.43(m, 2H), 7.28(m, 2H), 7.1 7(d, J=8.5 Hz, 2H), 4.99(d, J=11.9 Hz, 2H), 4.94(d, J=11.9 Hz, 2H), 4.63(dd, J=5.5, 0. 6 Hz, 2H), 4.52(dd, J=5.5, 0.6 Hz, 2H), 2.97(s, 6H);
$^{13}$C NMR(CDCl$_3$)δ 152.2, 134.2, 131.2, 130.9, 130.6, 128.1, 127.2, 126.0, 125.5, 1 25.5, 99.5, 56.9, 42.3

REFERENCE EXAMPLE 4
Preparation of 3,3'-bis(diphenylphosphinoylmethyl)-2,2'-bis(methoxymethyl)-1,1'-binaphthol 2.93 g (13.3 mmol) of diphenylphosphine oxide was dissolved in 40 ml of tetrahydrofuran and cooled to 0° C. Then, a solution comprising 1.4 g (15 mmol) of sodium t-butoxide and 20 ml of tetrahydrofuran was added thereto.

The mixture was stirred for 30 minutes, whereupon the solution became a white suspension.

This suspension was cooled to −40° C., and a solution comprising 2.5 g (5.3 mmol) of 3,3'-bis(chloromethyl)-2,2'-bis(methoxymethyl)-1,1'-binaphthol and 30 ml of tetrahydrofuran, was dropwise added thereto, and the mixture was gradually returned to room temperature.

After confirming disappearance of the starting materials, the mixture was neutralized with a saturated ammonium chloride aqueous solution and concentrated under reduced pressure until the amount of the solution became a half.

The solution was extracted with 80 ml of ethyl acetate, and the organic layer was washed with water (50 ml×2).

The aqueous layer was further extracted with ethyl acetate (50 ml×3), and the organic layers were put together and washed with a saturated sodium chloride aqueous solution (50 ml×2).

The washed organic layer was dried over anhydrous sodium sulfate, and then, the solvent was distilled off under reduced pressure. The residue was purified by silica gel flush column chromatography (methylene chloride:methanol= 30:1) to obtain 3.95 g (93%) of the above-identified compound.
$^1$H NMR(CDCl$_3$) δ 8.30(d, J=2.45 Hz, 2H), 7.92–7.76(m, 10H), 7.52–7.41(m, 12H), 7. 35(m, 2H), 7.15(m, 2H), 6.85 (d, J=8.55 Hz, 2H), 4.21(d, J=6.5 Hz, 2H), 4.20(d, J=6.5H z, 2H), 4.15(dd, J=13.5, 13.5 Hz, 2H), 4.01(dd, J=13.5, 13.5 Hz, 2H), 2.84(s, 6H)

REFERENCE EXAMPLE 5

Preparation of 3,3'-bis(1-hydroxy-2-diphenylphosphinoylethyl)-2,2'-bis(methoxymethyl)-1,1'-binaphthol 1.3 ml (1.95 mmol) of n-butyl lithium (1.56 N, n-hexane solution) was added to a solution comprising 422 mg (1.95 mmol) of methyldiphenylphosphine oxide and 15 ml of tetrahydrofuran, and the mixture was cooled to −78° C. and stirred for 1 hour.

A solution comprising 280 mg (0.65 mmol) of 3,3'-diformyl-2,2'-bis(methoxymethyl)-1,1'-binaphthol and 1.5 ml of tetrahydrofuran, was added thereto at −78° C. and stirred for 1 hour.

The mixture was returned to room temperature and further stirred for 1 hour, and then, it was neutralized with a saturated ammonium chloride aqueous solution and then extracted with ethyl acetate.

The organic layer was washed with water and a saturated sodium chloride aqueous solution and then dried over anhydrous sodium sulfate.

The solvent was distilled off under reduced pressure, and the residue was purified by silica gel column chromatography (acetone:methylene chloride=1:4) to obtain 579 mg (quantitative) of the above-identified compound as a slightly yellow amorphous product.

REFERENCE EXAMPLE 6

Preparation of 3,3'-bis(2-diphenylphosphinoyl-1-ethylene) 2,2'-bis(methoxymethyl)-1,1'-binaphthol A solution comprising 403 mg (0.468 mmol) of 3,3'-bis (1-hydroxy-2-diphenylphosphinoylethyl)-2,2'-bis (methoxymethyl)-1,1 -binaphthol and 2 ml of methylene chloride, was cooled with ice, and 0.46 ml (3.28 mmol) of triethylamine and 0.18 ml (2.34 mmol) of methanesulfonyl chloride, were added thereto.

The mixture was returned to room temperature and then stirred for 1 hour. Then, 0.7 ml (4.68 mmol) of DBU was added thereto, and the mixture was stirred overnight at room temperature.

Water was added thereto, and the mixture was extracted with methylene chloride.

The product was dried over anhydrous sodium sulfate, and the solvent was distilled off under reduced pressure. Then, the residue was purified by silica gel column chromatography (methanol:chloroform=1:19) to obtain 347 mg (90%) of the above-identified compound as a slightly yellow amorphous product.

REFERENCE EXAMPLE 7

Preparation of 3,3'-bis(2-diphenylphosphinoylethyl)-2,2'-bis(methoxymethyl)-1,1'-binaphthol 310 mg (0.375 mmol) of 3,3'-bis(2 -diphenylphosphinoyl-1-ethylene)-2,2'-bis(methoxymethyl)-1,1'-binaphthol was dissolved in a solution comprising 3 ml of methanol and 1 ml of ethyl acetate.

50 mg of 10% palladium-carbon was added thereto, and the mixture was stirred for 1 hour under a hydrogen stream.

10 ml of ethyl acetate was added thereto, followed by Celite filtration. Then, the solvent was distilled off under reduced pressure.

The residue was purified by silica gel column chromatography (methanol:chloroform=1:30) to obtain 281 mg of a slightly yellow oily substance.

This oily substance contained 22% of the above- identified compound and 72% of 3,3'-bis(2-diphenylphosphinoyl-1-ethylene)-2-methoxymethyl-1,1'-binaphthol having one of the methoxymethyl groups detached (3:10).

EXAMPLE 1

Preparation of Asymmetric Ligand 1 (3,3'-bis(diphenylphosphinynoylmethyl)-1,1'-binaphthol)

3.8 g (4.73 mmol) of 3,3'-bis(diphenylphosphinoylmethyl)-2,2'-bis(methoxymethyl)-1, 1'-binaphthol was dissolved in a solvent comprising 40 ml of methanol and 40 ml of methylene chloride.

A catalyst amount of p-toluenesulfonic acid monohydrate was added thereto, and the mixture was stirred overnight at 40° C.

The mixture was concentrated under reduced pressure and extracted with ethyl acetate.

The organic layer was washed with water (30 ml×2), and the aqueous layer was further extracted with ethyl acetate (30 ml×3).

The organic layers were put together and washed with a saturated sodium chloride aqueous solution, and then, it was dried over anhydrous sodium sulfate.

The solvent was distilled off under reduced pressure.

The obtained crude product was purified by recrystallization to obtain 3.0 g (89%) of the above-identified compound.
$^1$H NMR(CDCl$_3$) δ 7.80–7.67(m, 12H), 7.53–7.41(m, 12H), 7.24(m, 2H), 7.14(t, J=7. 65 Hz, 2H), 6.88(d, J=8.55 Hz, 2H), 4.06(dd, J=14.4, 14.4 Hz, 2H), 3.92(dd, J=14.4, 14 .4 Hz, 2H);
$^{13}$c NMR(CDCl$_3$)δ 151.4, 151.3, 133.2, 132.1(d, J=3.13 Hz), 132.1(d, J=2.13 Hz),1 31.9, 131.7, 131.5, 131.4, 131.1 (d, J=7.13 Hz), 131.0(d, J=7.13 Hz), 130.9, 129.0(d J=2.0 Hz), 128.7(d, J=3.13 Hz), 128.6(d, J=2.0 Hz), 127.7, 126.4, 124.8, 123. 6,121 .6, 121.5, 117.1, 34.0(d, J=66.8 Hz);
$^{31}$P NMR(CDCl$_3$) δ 37.94
$[\alpha]^{23}_D$+131.5° (c=1.0, CH$_3$OH)

EXAMPLE 2

Preparation of asymmetric ligand 2 (3.3'-bis(2-diphenylphosphinoyl-1-ethylene)-1,1'-binaphthol)

By an operation similar to Example 1, the above-identified compound was obtained in a yield of 48% from an oily substance comprising 3,3'-bis(2-diphenylphosphinoylethyl)-2,2'-bis(methoxymethyl)-1,1'-binaphthol and 3,3'-bis(2-diphenylphosphinonylethyl)-2-methoxymethyl-1,1'-binaphthol in a ratio of 3:10.

EXAMPLE 3

Preparation of Asymmetric Catalyst 1 Containing 4 mol Equivalent of Tri N-butylphosphine Oxide

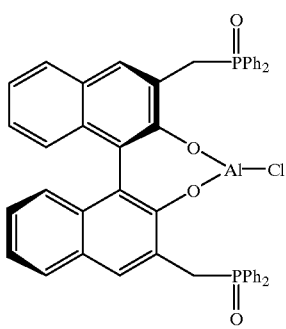

Asymmetric Catalyst 1

Into a flame-dried flask, 15 mg (68.8 μmol) of tri n-butylphosphine oxide was put and dried under reduced pressure at 80° C. for 2 hours.

0.1 ml of methylene chloride was added thereto, and 18 μl (17.28 μmol) of a 0.96 M n-hexane solution of ethylaluminum chloride was added thereto in an argon stream.

After stirring for 10 minutes, a solution comprising 13 mg (18.2 μmol) of asymmetric ligand 1 (3,3'-bis (diphenylphosphinynoylmethyl)-1,1'-binaphthol) and 0.35 ml of methylene chloride, was added thereto at room temperature.

The reaction solution was stirred at the same temperature for 1 hour, whereby it became a transparent solution.

This solution was employed directly for the preparation of the optically active cyanohydrin.

EXAMPLES 4 TO 8

By an operation similar to Example 3, solutions containing asymmetric catalyst 1 were prepared wherein the type and the amount of the phosphine oxide added were different.

| Example No. | Phosphine oxide added Structural formula | Amount (mole equivalent) |
|---|---|---|
| 4 | — | 0 |
| 5 | $Ph_3P(O)$ | 4 |
| 6 | $Ph_2P(O)CH_3$ | 4 |
| 7 | $n\text{-}Bu_3P(O)$ | 10 |
| 8 | $n\text{-}Oct_3P(O)$ | 4 |

EXAMPLE 9

Preparation of Asymmetric Catalyst 2

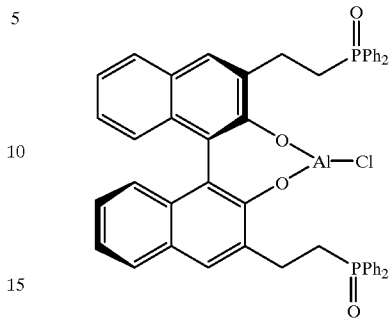

Asymmetric Catalyst 2

In an operation similar to Example 4, a solution containing the above-identified asymmetric catalyst, was prepared wherein asymmetric ligand 2 contains no phosphine oxide.

EXAMPLES 10 TO 19

Preparation of an Optically Active Cyanohydrin Compound

The solution containing asymmetric catalyst 1 was cooled to −40° C., and an aldehyde compound was added thereto. Trimethylsilylcyanide (1.8 mol equivalent to the aldehyde compound) was slowly added over a period of 10 hours by means of a syringe pump. (The melting point of trimethylsilylcyanide is from 11 to 12° C., and according, it should be dropwise added from the upper end of the flask which is believed to be at a temperature of at least 15° C.)

The reaction solution was stirred at the same temperature (−40° C.).

2N hydrochloric acid was added thereto, and the mixture was vigorously stirred at room temperature. Then, ethyl acetate was added thereto, and the mixture was further stirred for 30 minutes.

The organic layer was separated and washed with water.

The aqueous layer was extracted twice with ethyl acetate.

The organic layers were put together and washed with a saturated sodium chloride aqueous solution and then dried over anhydrous sodium sulfate.

The solvent was distilled off under reduced pressure, and then, the residue was purified by silica gel flush chromatography (n-hexane:ethyl acetate=10:1) to obtain the desired optically active cyanohydrin compound.

The results obtained by using various types of aldehyde compounds are shown in the following Table.

The yield of the product was determined by a conventional method by leading it to an acetate, a benzoyl ester, a p-nitrobenzoyl ester, an ethyl carbonate or a t-butyldimethylsilyl ether.

In the Table, the amount of the asymmetric catalyst is represented by mol % to the aldehyde compound, and the amount of the phosphine oxide is represented by mol equivalent to asymmetric catalyst 1.

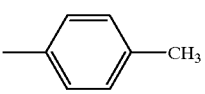

| Ex. No. | R | Amount of asymmetric catalyst (mol %) | Phosphine oxide Type | Amount (mol equivalent) | Reaction time | Yield | ee | S/R |
|---|---|---|---|---|---|---|---|---|
| 10 | —(CH$_2$)$_2$Ph | 9 | n-BuP(O) | 4 | 37 | 97 | 97 | S |
| 11 | —(CH$_2$)$_5$CH$_3$ | 9 | n-BuP(O) | 4 | 58 | 100 | 98 | S |
| 12 | —CH(CH$_3$)$_2$ | 9 | n-BuP(O) | 4 | 45 | 96 | 90 | S |
| 13 | —CH(CH$_2$CH$_3$)$_2$ | 9 | n-BuP(O) | 4 | 60 | 98 | 83 | S |
| 14 | —CH=CH(CH$_2$)$_3$CH$_3$ | 9 | n-BuP(O) | 4 | 58 | 94 | 97 | |
| 15 | —CH=CHPh | 9 | n-BuP(O) | 4 | 40 | 99 | 98 | S |
| 16 | —Ph | 10 | — | 0 | 36 | 91 | 87 | |
| 17 | —Ph | 9 | CH$_3$P(O)Ph$_2$ | 4 | 70 | 75 | 92 | S |
| 18 | 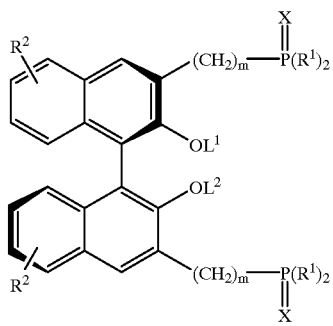 | 9 | CH$_3$P(O)Ph$_2$ | 4 | 70 | 87 | 90 | S |
| 19 | 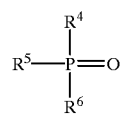 | 18 | CH$_3$P(O)Ph$_2$ | 4 | 70 | 86 | 95 | |

According to the method of the present invention, an industrially useful optically active cyanohydrin compound can readily be prepared in a high chemical yield and in a high optical yield.

What is claimed is:

1. An optically active binaphthyl compound of the formula (1):

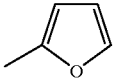

(1)

wherein R$^1$ is a C$_{1-6}$ alkyl group, an aryl group or an aryl C$_{1-6}$ alkyl group, X is an oxygen atom or a sulfur atom, R$^2$ is a hydrogen atom, a C$_{1-6}$ alkyl group, a C$_{2-6}$ alkenyl group, a C$_{2-6}$ alkynyl group or a halogen atom, each of L$^1$ and L$^2$ is a hydrogen atom, or L$^1$ and L$^2$ together form MY wherein M is a rare earth element or a Group 13 element, and Y is a C$_{1-6}$ alkoxy group, a C$_{1-6}$ alkylcarbonyloxy group or a halogen atom, and m is an integer of from 1 to 3.

2. The optically active binaphthyl compound according to claim 1, wherein R$^2$ is a hydrogen atom, and m is 1 or 2.

3. The optically active binaphthyl compound according to claim 2, wherein R$^1$ is a phenyl group.

4. The optically active binaphthyl compound according to claim 3, wherein each of L$^1$ and L$^2$ is a hydrogen atom.

5. The optically active binaphthyl compound according to claim 3, wherein L$^1$ and L$^2$ together form AlCl.

6. A method for producing an optically active cyanohydrin compound of the formula (3):

(3)

wherein R$^3$ is a C$_{1-6}$ alkyl group, an aryl group, an aryl C$_{1-6}$ alkyl group, a C$_{2-6}$ alkenyl group, an aryl C$_{2-6}$ alkenyl group, a C$_{2-6}$ alkynyl group, an aromatic heterocyclic group or a non-aromatic heterocyclic group, which comprises reacting an aldehyde compound of the formula (2):

R$^3$CHO  (2)

wherein R$^3$ is as defined above, with trimethylsilylcyanide in the presence of the optically active binaphthyl compound of the formula (1) as defined in claim 1 wherein L$^1$ and L$^2$ together form MY wherein M and Y are as defined above.

7. The method for producing an optically active cyanohydrin compound according to claim 6, wherein a phosphine oxide of the formula (4):

(4)

wherein each of R$^4$, R$^5$ and R$^6$ which are independent of one another, is a C$_{1-8}$ alkyl group, an aryl group or an aryl C$_{1-6}$ alkyl group, is added to the reaction system.

8. The method for producing an optically active cyanohydrin compound according to claim 7, wherein the optically active binaphthyl compound of the formula (1) wherein $R^2$ is a hydrogen atom, and m is 1 or 2, is used.

9. The method for producing an optically active cyanohydrin compound according to claim 8, wherein the optically active binaphthyl compound of the formula (1) wherein $R^1$ is a phenyl group, is used.

10. The method for producing an optically active cyanohydrin compound according to claim 9, wherein the optically active binaphthyl compound of the formula (1) wherein $L^1$ and $L^2$ together form AlCl, is used.

11. The method for producing an optically active cyanohydrin compound according to claim 10, wherein the aldehyde compound of the formula (2) wherein $R^3$ is $(CH_2)_2Ph$, $CH(CH_3)_2$, Ph, $(CH_2)_5CH_3$, $CH(CH_2CH_3)_2$, $CH=CH(CH_2)_3CH_3$, $CH=CHPh$, $C(CH_3)_2CH_2Ph$, a cyclohexyl group, a p-methylphenyl group or a 2-furyl group, is used.

12. The method for producing an optically active cyanohydrin compound according to claim 11, wherein the phosphine oxide of the formula (4) wherein each of $R^4$, $R^5$ and $R^6$ which are independent of one another, is $CH_3$, $(CH_2)_3CH_3$, $(CH_2)_7CH_3$ or Ph, is used.

* * * * *